United States Patent
O'Brien et al.

(10) Patent No.: US 10,575,818 B2
(45) Date of Patent: Mar. 3, 2020

(54) SYSTEMS AND METHODS FOR GEL MANAGEMENT

(71) Applicant: Neural Analytics, Inc., Los Angeles, CA (US)

(72) Inventors: Michael O'Brien, Los Angeles, CA (US); Mina Ranjbaran, Los Angeles, CA (US)

(73) Assignee: Neural Analytics, Inc., Los Angeles, CA (US)

( * ) Notice: Subject to any disclaimer, the term of this patent is extended or adjusted under 35 U.S.C. 154(b) by 0 days.

(21) Appl. No.: 16/215,451

(22) Filed: Dec. 10, 2018

(65) Prior Publication Data

US 2019/0175144 A1 Jun. 13, 2019

Related U.S. Application Data

(60) Provisional application No. 62/596,714, filed on Dec. 8, 2017.

(51) Int. Cl.
*A61B 8/00* (2006.01)
*A61B 8/08* (2006.01)

(52) U.S. Cl.
CPC .......... *A61B 8/4281* (2013.01); *A61B 8/0816* (2013.01); *A61B 8/4218* (2013.01); *A61B 8/4416* (2013.01); *A61B 8/4483* (2013.01); *A61B 8/54* (2013.01)

(58) Field of Classification Search
CPC ... A61B 8/4281; A61B 8/0816; A61B 8/4218; A61B 8/4416; A61B 8/4483; A61B 8/54
See application file for complete search history.

(56) References Cited

U.S. PATENT DOCUMENTS

| | | | |
|---|---|---|---|
| 4,429,577 A | 2/1984 | Sorenson et al. | |
| 6,261,249 B1* | 7/2001 | Talish | A61B 8/4227 600/459 |
| 2008/0021317 A1* | 1/2008 | Sumanaweera | A61B 8/4218 600/437 |
| 2008/0146970 A1 | 6/2008 | Litman et al. | |
| 2010/0298744 A1 | 11/2010 | Altshuler et al. | |
| 2015/0373286 A1* | 12/2015 | Matsuoka | G06T 5/50 348/165 |
| 2016/0071280 A1* | 3/2016 | Salahat | G06K 9/342 382/103 |
| 2017/0188994 A1 | 7/2017 | Flores et al. | |

FOREIGN PATENT DOCUMENTS

WO WO-2017/165425 A1 9/2017

OTHER PUBLICATIONS

Conti, et al., "Interface Design and Control Strategies for a Robot Assisted Ultrasonic Examination System", Experimental Robotics, pp. 97-113, Jan. 1, 2014 (Jan. 1, 2014).
International Search Report and Written Opinion dated Apr. 1, 2019, from application No. PCT/US2018/064783.
Vionnet, et al., "24-MHz Scanner for Optoacoustic Imaging of Skin and Burn", IEEE Transactions on Medical Imaging, vol. 33, No. 2, Feb. 2014.

* cited by examiner

*Primary Examiner* — Michael T Rozanski
(74) *Attorney, Agent, or Firm* — Foley & Lardner LLP

(57) ABSTRACT

Arrangements described herein relate to systems, apparatuses, and methods for managing gel on a subject to provide gel on a first area of the subject, including controlling a transducer to move to a second area of the subject and controlling the transducer to move the gel to the first area from the second area.

21 Claims, 7 Drawing Sheets

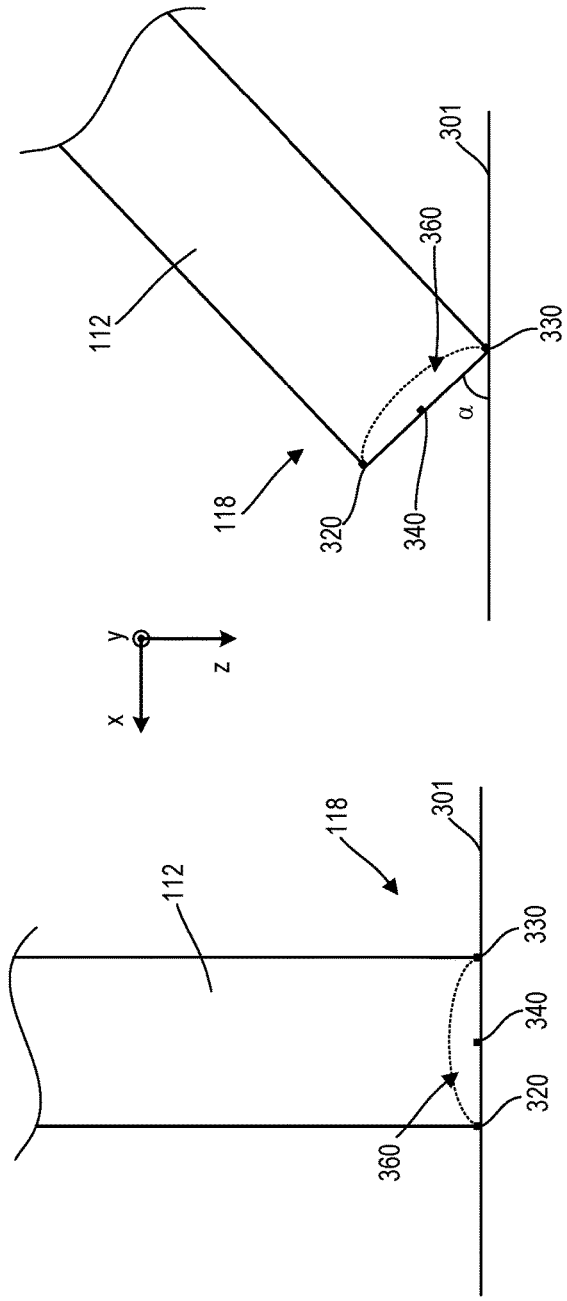
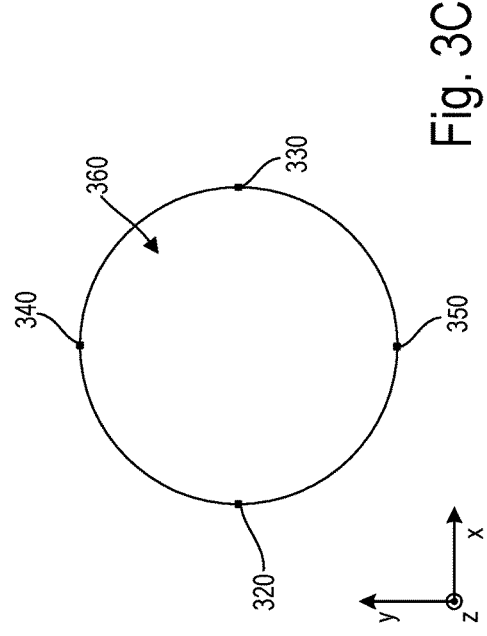
Fig. 3A
Fig. 3B
Fig. 3C

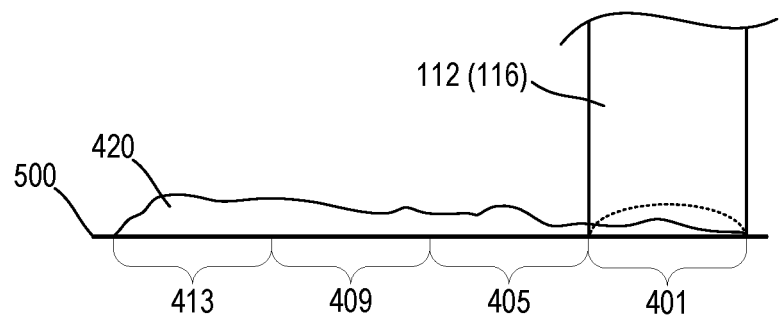
Fig. 5A
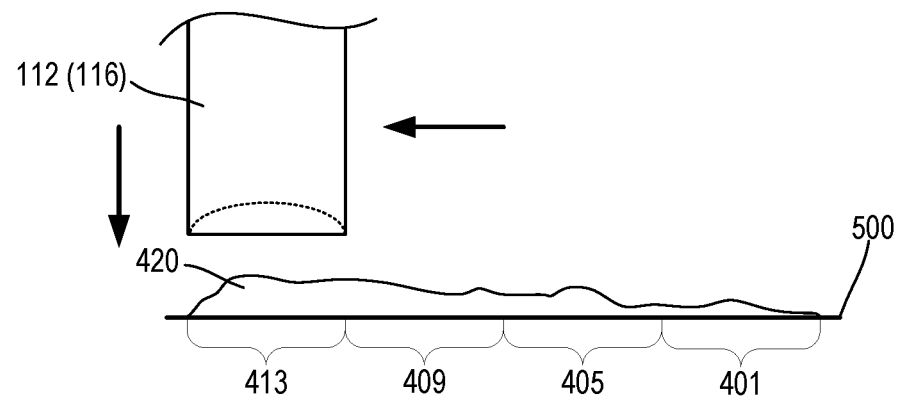
Fig. 5B
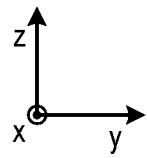

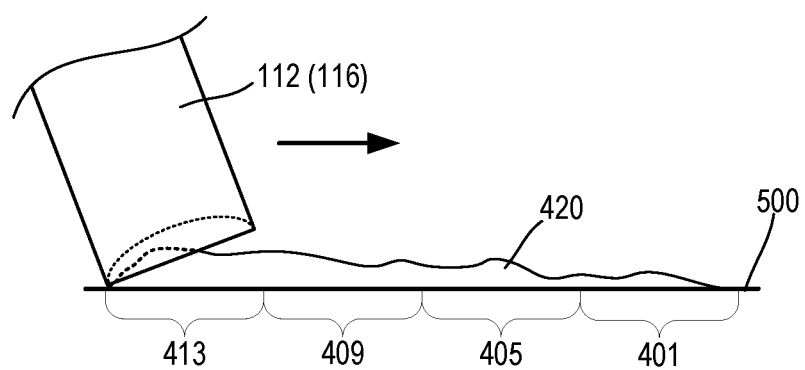
Fig. 5C
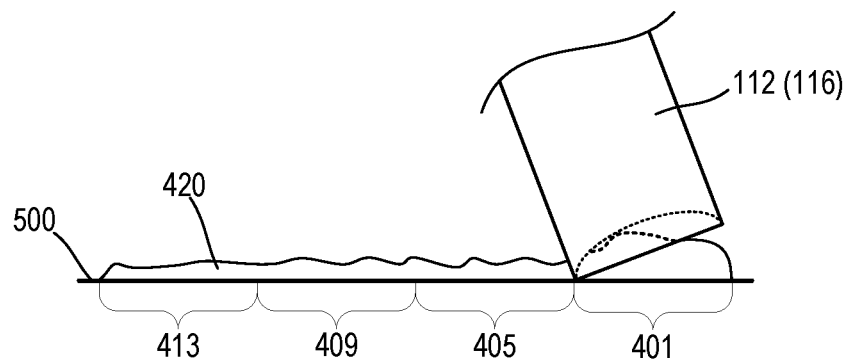
Fig. 5D
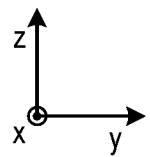

SYSTEMS AND METHODS FOR GEL MANAGEMENT

CROSS-REFERENCE TO RELATED PATENT APPLICATION

This application claims priority from provisional U.S. Application No. 62/596,714, filed Dec. 8, 2017, which is incorporated herein by reference in its entirety.

BACKGROUND

A gel can be applied to a skin of a subject to improve transmission of energy emitted by devices such as but not limited to, an ultrasound device (e.g., a Transcranial Doppler (TCD) device). The gel can be initially applied manually by an operator or automatically by the device in any suitable manner. In some situations, the gel may be lacking in some areas of the scanning surface for various reasons (e.g., due to the device spreading the gel during operation). Accordingly, an area that is covered by an insufficient amount of gel may degrade the performance of the device (e.g., by failure of transmission of energy waves).

SUMMARY

In some arrangements, a system for managing gel on a subject includes a transducer and a controller configured to control the transducer to move the gel to a first area of the subject to a second area of the subject.

In some arrangements, the system further includes a sensor configured to output a gel sufficiency parameter for the gel on the subject. The controller is configured to determine that a first amount of the gel on the first area is insufficient based on the gel sufficiency parameter. The controller is configured to move a second amount of the gel to the first area from the second area in response to determining that the first amount of gel on the first area is insufficient.

In some arrangements, the controller is configured to determine that the second amount of gel on the second area is above a threshold.

In some arrangements, the system further includes a camera configured to capture image data of the second area, wherein the controller is further configured to determine that the second amount of gel on the second area is above an infrared (IR) reflective signature threshold based on an IR reflective signature information determined based on the image data.

In some arrangements, the system further includes a camera configured to capture image data of the second area, wherein the controller is further configured to determine that the second amount of gel on the second area is above a maximally stable extremal regions (MSER) threshold based on MSER information determined based on the image data.

In some arrangements, the controller determines that the first amount of the gel on the first area is insufficient responsive to determining that the gel sufficiency parameter is below a threshold.

In some arrangements, the gel sufficiency parameter is a resistance between two metal contacts of the sensor.

In some arrangements, the gel sufficiency parameter is a conductance or conductivity between two metal contacts of the sensor.

In some arrangements, the sensor is on the transducer.

In some arrangements, the system further includes robotics configured to move the transducer. The controller is configured to control the transducer to move the gel by controlling the robotics to translate the transducer from the second area to the first area.

In some arrangements, the controller configures the robotics to translate the transducer from the second area to the first area by controlling the robotics to move the transducer to be over the second area, extend the transducer toward the subject in response to the controller determining that the transducer is over the second area, orient a gel retaining surface of the transducer to face a direction of the first area by tilting the transducer to a tilted position, and move the transducer from the second area to the first area while the transducer is in the tilted position.

In some arrangements, the controller configures the robotics to translate the transducer from the second area to the first area by controlling the robotics to tilt the transducer in a tilted position while the transducer is in the second area and moving the transducer to the first area in the tilted position while contacting the subject.

In some arrangements, the controller configures the robotics to translate the transducer from the second area to the first area by controlling the robotics to move the transducer from the second area to the first area across the object.

In some arrangements, a workspace of the transducer comprises a plurality of areas. The plurality of areas includes the first area and the second area.

In some arrangements, the workspace corresponds to a temporal region of a head of the subject.

In some arrangements, the plurality of areas corresponds to steps by which the transducer is configured to move.

In some arrangements, the controller selects the second area randomly from the plurality of areas.

In some arrangements, the second area is a gel reservoir.

In some arrangements, a method for managing gel on a subject includes providing a transducer and controlling the transducer to move the gel to a first area of the subject from a second area of the subject.

In some arrangements, controlling the transducer to move the gel to the first area from the second area includes moving the transducer to be over the second area, extending the transducer toward the subject in response to the controller determining that the transducer is over the second area, orienting a gel retaining surface of the transducer to face a direction of the first area by tilting the transducer to a tilted position, and moving the transducer from the second area to the first area while the transducer is in the tilted position.

In some arrangements, a non-transitory computer-readable medium having computer-readable instructions, such that when executed, causes a processor of a controller to provide gel on a first area of a subject by controlling the transducer to move to a second area of the subject and controlling the transducer to move the gel to the first area from the second area.

BRIEF DESCRIPTION OF THE FIGURES

Features and aspects of the present disclosure will become apparent from the following description and the accompanying example arrangements shown in the drawings, which are briefly described below.

FIG. 3A is a schematic diagram illustrating a probe having a sensor according to various arrangements.

FIG. 3B is a schematic diagram illustrating a probe having a sensor according to various arrangements.

FIG. 3C is a schematic diagram illustrating a probe having a sensor according to various arrangements.

FIGS. 5A-5D are schematic diagrams illustrating an example method for managing gel according to various arrangements.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Figure 1:
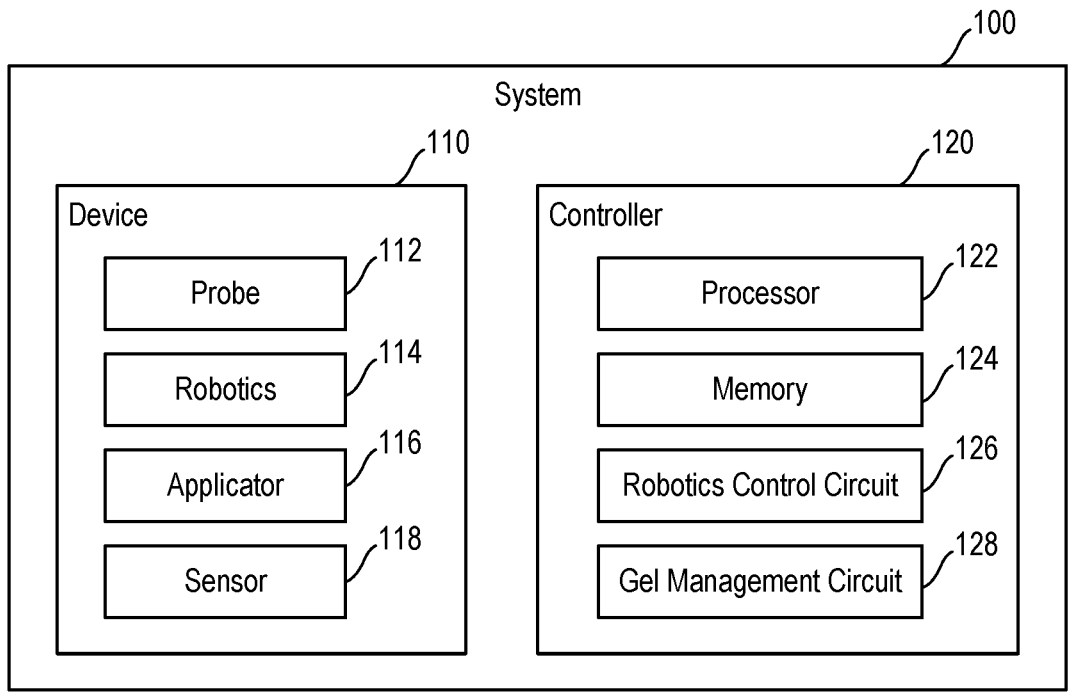
FIG. 1 is a block diagram of a system according to various arrangements.

FIG. 1 illustrates a block diagram of a system 100 according to various arrangements. Referring to FIG. 1, the system 100 includes at least a device 110 and a controller 120. In some arrangements, the system 100 is used in conjunction with a medical device for use with respect to a subject's head (e.g., a device for monitoring neurological activity, a surgical device, a device for monitoring radioactive traces, or any other appropriate device). In other arrangements, the system 100 can be used in conjunction with a medical device for use with respect to another body part of the subject.

In some arrangements, the device 110 includes a probe (e.g., a transducer) 112 and robotics 114 configured to control the probe 112, collectively referred to as an "instrument." In that regard, "instrument" as used herein refers to at least one data collection device (e.g., a probe such as but not limited to, the probe 112) and devices (e.g., positioning components such as but not limited to, the robotics 114) configured to control position and operations (e.g., data collection) of the data collection device. For example, the robotics 114 are configured to translate the probe 112 along a surface of the skin of the subject and to move the probe 112 toward and away from the head. In some arrangements, an end of the probe 112 interfaces with the robotics 114. The robotics 114 include components such as but not limited to, a motor assembly and so on for controlling the probe 112 (e.g., control z-axis pressure, normal alignment, or the like of the probe 112). In some arrangements, the registration of the probe 112 against the subject is accomplished using the robotics 114 to properly position and align the probe 112 with anatomic locations/areas of the subject.

In some arrangements, the probe 112 includes a first end and a second end that is opposite to the first end. In some arrangements, the first end includes a concave surface that is configured to be adjacent to or to contact a scanning surface (e.g., the skin of the subject). The concave surface is configured with a particular pitch to focus generated energy towards the scanning surface. In some arrangements, the device 110 is a Transcranial Doppler (TCD) apparatus such that the first end of the probe 112 is configured to be adjacent to or to contact and align along a human head (e.g., a side of the human head), and the first end of the probe 112 is configured to provide ultrasound wave emissions from the first end and directed into the human head (e.g., towards the brain). In that regard, the probe 112 is an ultrasound probe configured for ultrasound procedures. In other arrangements, the probe 112 is configured to emit other types of waves during operation, such as, but not limited to, infrared, x-rays, electromagnetic, thermal, near-infrared, optical, lighting, audio, electroencephalography, or the like.

In some arrangements, the second end of the probe 112 is coupled to the robotics 114. In some arrangements, the second end of the probe 112 includes a threaded section along a portion of the body of the probe 112, and the second end is configured to be secured in the robotics 114 via the threads (e.g., by being screwed into the robotics 114). In other arrangements, the probe 112 is secured in the robotics 114 by any other suitable connecting mechanisms such as but not limited to, welding, adhesive, one or more hooks and latches, one or more separate screws, press fittings, or the like.

Further disclosure regarding probe systems that can be used in conjunction with the systems described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety.

The device 110 further includes an applicator 116 configured to apply and/or re-apply gel to the skin of the subject. The gel is an ultrasonic coupling gel used to enhance comfort of the patient and to improve transmission of the ultrasonic waves (from the probe 112) through the epidermis and dermis (skin). In some examples, the gel can be an ultrasound gel used in connection with ultrasound emitting devices (e.g., TCD devices). In other examples, the gel may be another suitable gel, liquid, powder, composite material, or the like, for other types of procedures. The gel may have suitable viscosity such that the gel sticks to the skin after being applied to the skin, and that the gel can be translated or otherwise moved by the applicator 116.

In some arrangements, the applicator 116 is the body of the probe 112 itself. Such an arrangement minimizes a number of components of the device 110 and a size of the device 110. In such examples, the robotics 114 are configured to move the probe 112 (the applicator 116) to reapply the gel in the manner described. Additional robotics to separately move the applicator 116 may not be needed.

In some arrangements, the applicator 116 is different from the probe 112 (i.e., is not the body of the probe 112 itself). The applicator 116 is shaped to collect the gel and to translate the gel from one area of the skin to another area of the skin. For example, the applicator 116 may have one or more suitable surfaces and edges configured to collect and retain the gel in one area of the skin and move the gel to another area of the skin. In that regard, the applicator 116 may have a cone shape, a skirt shape, a bell shape, a flat shape, a scoop shape, and angled surface, and so on.

In some examples, the applicator 116 can be made from a soft, flexible, or resilient material, such as but not limited to, closed cell foam, open cell foam, self-skinning open or closed cell foams, cast, aerated, or extruded silicone or urethane, polyurethane, and so on. In other examples, the applicator 116 can be made from a rigid material such as but not limited to, metal, metal alloy, carbon fiber, and so on.

In some arrangements, the applicator 116 is attached to and fixed to a housing of the probe 112, such that the applicator 116 can move with the probe 112. The robotics 114 are configured to move the applicator 116 indirectly by moving the probe 112.

In some arrangements, the applicator 116 is separate from the probe 112 and does not move with the probe 112. In such arrangements, additional robotics (not shown) different from the robotics 114 are configured to move the applicator 116 independently to reapply the gel in the manner described.

The device 110 further includes a sensor 118 configured to detect and monitor an amount of gel present on the skin of the subject. The sensor 118 is configured to output a gel sufficiency parameter for the gel on the skin of the subject. The gel sufficiency parameter is indicative of the amount of gel present on the skin. As discussed in further detail herein, one or more areas of the skin may have gel applied thereon. A gel sufficiency parameter can be outputted by the sensor 118 for each area on which the gel is applied.

In some examples, the sensor 118 is configured to measure a resistance between two contact points (e.g., between two metal contacts) of the sensor 118. In that regard, the sensor 118 can be an ohmmeter configured to output a signal indicative of the gel sufficiency parameter (e.g., the resistance between the two contact points). In some examples, the sensor 118 is configured to measure a capacitance between two contact points (e.g., between two metal contacts) of the sensor 118. In that regard, the sensor 118 can be a capacitance meter configured to output a signal indicative of the gel sufficiency parameter (e.g., the capacitance between the two contact points).

In some examples, the sensor 118 is disposed on the applicator 116. In some examples, the sensor 118 is disposed on the probe 112. In other examples, the sensor 118 is disposed on another suitable structure of the device 110 to collect the gel sufficiency parameter in the manner described.

In some arrangements, the system 100 includes a controller 120 for controlling operations, processing data, executing input commands, providing results, and the like with respect to the system 100. For example, the controller 120 is configured to control the device 110 to execute commands, receive data from the device 110 (e.g., the physiological data from the probe 112 and the gel sufficiency parameter from the sensor 118), and control the applicator 116 to reapply the gel in the manner described, and so on. In some arrangements, the controller 120 includes a processor 122, memory 124, a robotics control circuit 126, and a gel management circuit 128.

In some arrangements, the processor 122 is implemented as a general-purpose processor and is coupled to at least one memory 124. The processor 122 includes any suitable data processing device, such as a microprocessor. Alternatively, the processor 122 includes any suitable electronic processor, controller, microcontroller, or state machine. In some arrangements, the processor 122 is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 122 is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 124 includes a non-transitory processor-readable storage medium that stores processor-executable instructions. In some arrangements, the memory 124 includes any suitable internal or external device for storing software and data. Examples of the memory 124 can include, but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 124 can store an Operating System (OS), user application software, and/or executable instructions. The memory 124 can also store application data, such as an array data structure. In some arrangements, the memory 124 stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

The robotics control circuit 126 can be implemented with the processor 122 and the memory 124. The robotics control circuit 126 is operatively coupled to the robotics 114 (e.g., via suitable wires or wireless interface) and is configured to control the robotics 114 to move the probe 112 to collect physiological data (e.g., the ultrasound data) of the subject. For example, the robotics control circuit 126 is configured to move the probe 112 within a workspace of the probe 112. In the examples in which the applicator 116 is the probe 112 itself or the examples in which the applicator 116 is attached/fixed to the probe 112 such that the applicator 116 can move with the probe 112, the robotics control circuit 126 is capable of configuring the robotics 114 to move the applicator 116 to reapply the gel in the manner described. In the examples in which the applicator 116 moves independently with respect to the probe 112, the robotics control circuit 126 is capable of configuring dedicated robotics (different from the robotics 114) to move the applicator 116 to reapply the gel in the manner described.

The gel management circuit 128 can be implemented with the processor 122 and the memory 124. The gel management circuit 128 is configured to receive the gel sufficiency parameter from the sensor 118, determine that an amount of gel on an area of the skin is insufficient based on the gel sufficiency parameter, and so on. In that regard, the gel management circuit 128 is operatively coupled to the sensor 118 via suitable wires or wireless interface. The gel management circuit 128 is operatively coupled to the robotics control circuit 126 for exchanging data.

In some arrangements, the system 100 may further include a cradle (not shown) configured to receive and support a part of the subject such as but not limited to, the subject's head, during operation of the probe 112. The cradle is capable of accommodating and supporting different head sizes for use in conjunction with the device 110. In some arrangements, the system 100 may further include a camera (not shown) configured to capture one or more images of the subject (e.g., the subject's head) when the subject's head is placed within the cradle. From the captured one or more images, the subject's head can be registered with respect to the device 110. That is, the device 110 can initially position or align the probe 112 for subsequent operations on the subject's head, restricting or defining the workspace of the probe 112 to certain boundaries during operation of probe 112, and so on.

In some arrangements, the system 100 as described herein is used in conjunction with other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hyrdrocephalus, anoxic insults, and so on), ophthamological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and the like.

In some arrangements, the system 100 as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and the like), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and the like. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and the like.

Figure 2:
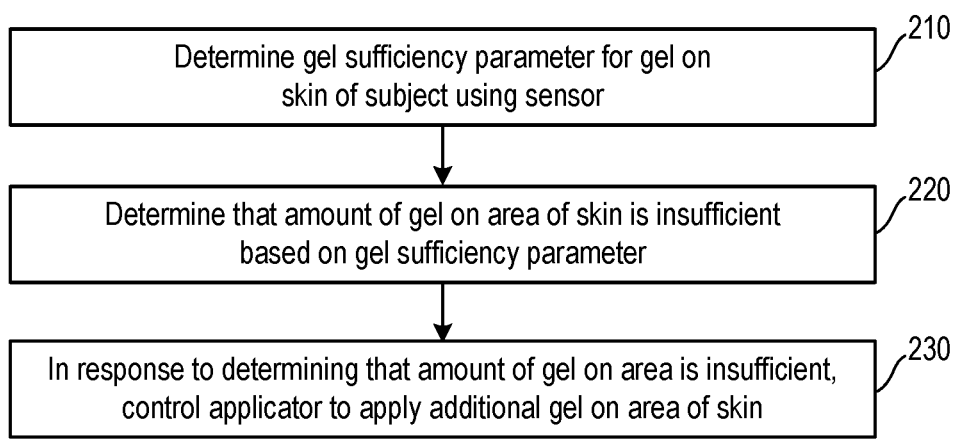
FIG. 2 is a flowchart diagram illustrating an example method for managing gel on a subject according to various arrangements.

FIG. 2 is a flowchart diagram illustrating an example method 200 for managing gel on a skin of a subject according to various arrangements. Referring to FIGS. 1-2, the method 200 is concerned with detecting a lack of gel in an area of the skin after the gel is applied and controlling the applicator 116 to apply additional gel to that area as a response.

At 210, the sensor 118 is configured to determine and output a gel sufficiency parameter for the gel on the skin of the subject. The gel sufficiency parameter is outputted to the gel management circuit 128 of the controller 120. As described, in some examples, the gel sufficiency parameter is a signal indicative of the resistance between two contact points of the sensor 118. In some examples, the gel sufficiency parameter is a signal indicative of the conductance (which is a multiplicative inverse or reciprocal of resistance) or conductivity (which is a multiplicative inverse or reciprocal of resistivity) between the two contact points of the sensor 118. In some examples, the gel sufficiency parameter is a signal indicative of the capacitance between two contact points of the sensor 118.

FIG. 3A is a schematic diagram illustrating the probe 112 having the sensor 118 according to various arrangements. FIG. 3B is a schematic diagram illustrating the probe 112 having the sensor 118 according to various arrangements. FIG. 3C is a front schematic view of the probe 112 having the sensor 118 according to various arrangements. Referring to FIGS. 1-3C, the sensor 118 includes contacts 320-350. For example, the contacts 320-350 can be metal and function like electrodes. The metal contacts 320-350 are located on an outer edge of a concave surface 360 of the probe 112. While the metal contacts 320-350 are shown to be evenly distributed on a diameter of the concave surface 360, the metal contacts 320-350 can be located anywhere on the outer edge of the concave surface 360, or any other position along the probe 112 such that the metal contacts 320-350 do not interfere with acoustic energy transmitted or received by the probe 112. While four metal contacts 320-350 are depicted in FIGS. 3A-3C, the sensor 118 may include any number of metal contacts. For example, the sensor 118 can include just one contact to determine the presence or absence of gel. As another example, the sensor 118 can include more than four contacts, such as eight contacts evenly spaced along the perimeter of the surface 360 so that any one or more pairs of contacts that are paired across the diameter of the surface 360 can be utilized to determine the gel sufficiency parameter. As described, the concave surface 360 is configured with a particular pitch to focus generated energy towards the scanning surface (e.g., the skin 301).

The sensor 118 can output resistance, conductance, conductivity, or capacitance between any two of the metal contacts 320-350. In that regard, the sensor 118 includes one or more of a voltage/current source, an ohmmeter, a voltmeter, an ammeter, a capacitance meter, a multimeter, and so on for determining one or more of the resistance, conductance, conductivity, and capacitance between any pair of the metal contacts 320-350 in any suitable manner. That is, the resistance, conductance, conductivity, or capacitance measured between two of the metal contacts 320-350 is expected to account for the resistance, conductance, conductivity, or capacitance of the gel if the gel is present between the two of the metal contacts 320-350. For example, if the sensor 118 outputs a conductance or conductivity parameter that indicates that there is good conductance or conductivity between one or more pairs of the metal contacts 320-350 (e.g., based on the threshold described with respect to block 220), the gel management circuit 128 can determine that the gel is present.

The resistance, conductance, conductivity, or capacitance between any pair of the metal contacts 320-350 may depend on orientation of the probe 112 in some examples. The robotics control circuit 126 is configured to control the robotics 114, and therefore keeps track of the orientation of the probe 112. FIG. 3A illustrates a scenario in which the probe 112 is positioned to be perpendicular to skin 301 of a subject. In other words, the probe 112 extends in the z-axis or in a direction parallel to the z-axis. As shown, all of the metal contacts 320-350 are in contact with the skin 301 when the probe 112 is perpendicular to the skin 301. Therefore, in the scenario illustrated by FIG. 3A, the resistance, conductance, conductivity, or capacitance between any pair of the metal contacts 320-350 may be weighted equally. That is, although the resistance, conductance, conductivity, or capacitance measured between one pair of the metal contacts 320-350 can be used for sufficiency assessment at block 220 (because any combination of the metal contacts 320-350 is weighted equally), the resistance, conductance, conductivity, or capacitance measured between one or more additional pairs of the metal contacts 320-350 can also be used to check against the threshold to provide additional comfort level in determining whether the gel is or is not sufficient.

FIG. 3B illustrates a scenario in which the probe 112 is positioned to be oblique to the skin 301. That is, the probe 112 is positioned by the robotics 114 to be neither perpendicular nor parallel to the skin 301. In other words, the probe 112 extends in a direction that traverses the z-axis. As shown, the metal contact 330 is in contact with the skin 301 when the probe 112 is oblique to the skin 301. Although the metal contacts 340 and 350 (not shown in view) may be floating (spaced apart from the skin) in some cases, the metal contacts 340 and 350 may still be in contact with the skin 301 when the portion of the probe 112 with the metal contact 330 pushes slightly deeper into the skin 301, which may often be the case. This is because an angle of incidence $\alpha$ of the probe 112 may be small (e.g., less than 20°). The metal contact 320 may be farther from the skin 301 than the metal contacts 340 and 350.

In other words, the resistance, conductance, conductivity, or capacitance measured between the metal contact 320 and another one of the metal contacts 330-350 may be ignored in some circumstances when the probe 112 is oblique to the skin 301. The weights described herein may depend (e.g., inversely proportional to) on the angle of incidence $\alpha$, e.g., when the angle of incidence $\alpha$ is small, the resistance, conductance, conductivity, or capacitance measured between the metal contact 320 and another one of the metal contacts 330-350 can be used for comparing against the threshold at block 220. When the angle of incidence $\alpha$ is large (e.g., above a threshold such as but not limited to, 10°, 15°, or 18°), the resistance, conductance, conductivity, or capacitance measured between the metal contact 320 and another one of the metal contacts 330-350 is ignored at block 220.

A scalar can be multiplied with the resistance, conductance, conductivity, or capacitance measured between each pair of the metal contacts 320-350 to provide the weighting as described. The scalar can be either 0 and 1. The scalar being 0 means that the resistance, conductance, conductivity, or capacitance is being ignored. This may be the case for the resistance, conductance, conductivity, or capacitance measured between the metal contact 320 and another one of the metal contacts 330-350 when the angle of incidence α exceeds the threshold as described. The scalar being 1 means that the resistance, conductance, conductivity, or capacitance is being taken entirely into account. The scalar for the resistance, conductance, conductivity, or capacitance measured between the metal contacts 330 and 340, the contacts 330 and 350, and the metal contacts 340 and 350 may always be 1 in some examples when the angle of incidence α is above 0°. When the angle of incidence α is 0° (no tilt), the scenario described relative to FIG. 3A is applicable (e.g., the scalar is 1 for every pair of the metal contacts 320-350).

In other examples not shown, another metal contact can be disposed on part of the concave surface 360 that is within a boundary defined by the outer edge on which the metal contacts 320-350 are located. In some examples, such a metal contact is at a center of the concave surface 360. In other examples, such a metal contact can be anywhere within the boundary defined by the outer edge.

Figure 4:
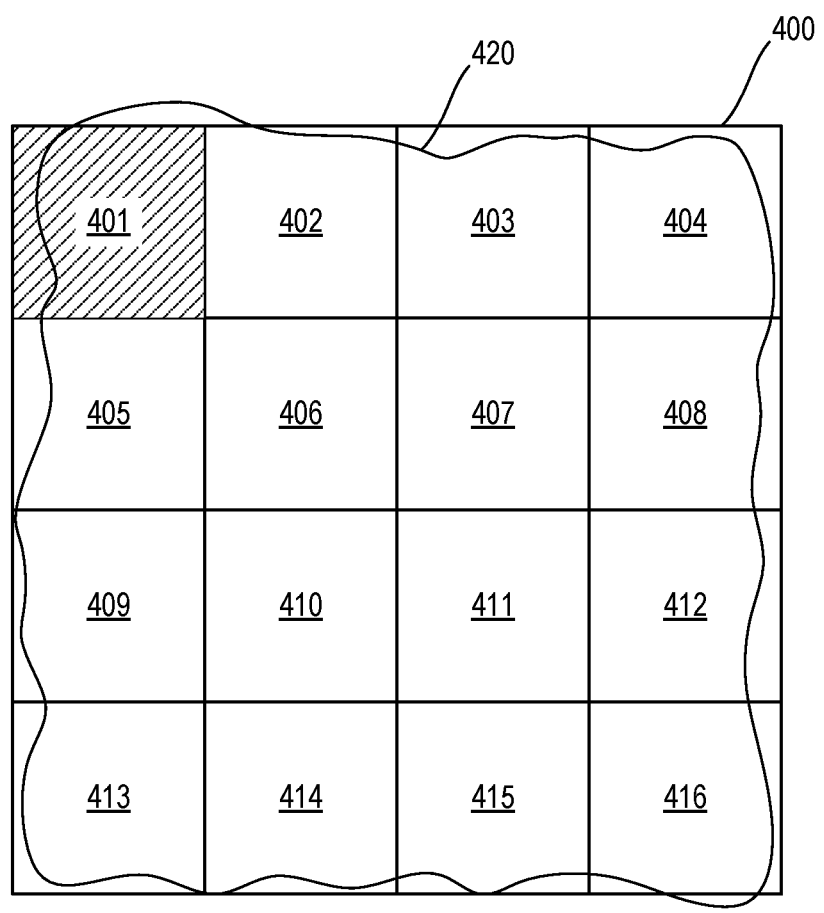
FIG. 4 is a schematic diagram illustrating areas in which gel can be applied according to various arrangements.

In some examples, the sensor 118 is configured to monitor gel quantity information with respect to various areas in a workspace of the probe 112 by determining a gel sufficiency parameter for each area in the workspace. FIG. 4 is a schematic diagram illustrating areas 401-416 in which gel 420 is applied according to various arrangements. Referring to FIGS. 1-4, as shown in FIG. 4, a workspace 400 of the probe 112 may correspond to a maximum allowable boundary which the robotics 114 can move the probe 112. The robotics 114 may not be able to move the probe 112 beyond the workspace 400 (e.g., due to the design of the robotics 114 or due to the self-imposed restrictions determined during a registration process with respect to a subject). The boundary bounds a scanning workspace, which corresponds to anatomical features of interest (such as but not limited to, a temporal region) of the subject. The scanning workspace may be determined based on suitable registration process. Further disclosure regarding the registration process that can be used in conjunction with the systems described herein can be found in non-provisional patent application Ser. No. 16/132,068, titled SYSTEMS AND METHODS FOR REGISTERING HEADSET SYSTEM, and filed on Sep. 14, 2018, which is incorporated herein by reference in its entirety.

While shown to be planar (e.g., in an XY-plane), the workspace 400 can be 3-dimensional (in an XYZ-space). While the workspace 400 and the areas 401-416 are shown to be squares, the workspace 400 and the areas 401-416 can have any suitable shape such as but not limited to, triangles, rectangles, circles, pentagons, hexagons, irregular shapes, and so on. The workspace 400 can be overlaid across a surface of a portion of the patient (e.g., the surface of the temporal region of the head of the patient).

The robotics 114 are configured by the robotics control circuit 126 to move the probe 112 within the workspace 400. In some examples, each of the areas 401-416 corresponds to a discrete step by which the probe 112 is configured to move. The probe 112 can be moved from a center of one of the areas 401-416 to a center of an adjacent one of the areas 401-416. The probe 112 does not stop between the centers of two adjacent ones of the areas 401-416 to collect any physiological data. As an example, the robotics 114 are configured by the robotics control circuit 126 to move the probe 112 from the center of the area 401, then to the center of the area 402, then to the center of the area 403, then to the center of the area 404, then to the center of the area 408, and so on.

In the examples in which the sensor 118 is attached/fixed to the probe 112 (e.g., as shown in FIGS. 3A and 3B), the sensor 118 can also be moved from one of the areas 401-416 to another one of the areas 401-416, as the sensor 118 moves with the probe 112. In the examples in which the applicator 116 is the probe 112 or is attached/fixed to the probe 112, the applicator 116 can also be moved from one of the areas 401-416 to another one of the areas 401-416, as the sensor 118 moves with the probe 112.

In some examples, the robotics 114 are configured by the robotics control circuit 126 to move the sensor 118 (by moving the probe 112 on which the sensor 118 is attached) throughout the workspace 400 (e.g., through the areas 401-416 in any suitable sequence) in a step-by-step manner to determine the gel sufficiency parameter with respect to each of the areas 401-416, before the probe 112 collects the physiological data of the subject or between a set number of iterations of the probe 112 collecting the physiological data of the subject (e.g., two iterations). In such examples, the probe 112 is not collecting the physiological data while the sensor 118 is determining the gel sufficiency parameter. This approach assures that the gel 420 is appropriately applied before the probe 112 begins to collect the physiological data, thus improving data accuracy.

In other examples, the robotics 114 is configured by the robotics control circuit 126 to move the sensor 118 (by moving the probe 112 on which the sensor 118 is attached) throughout the workspace 400 (e.g., through the areas 401-416 in any suitable sequence) in a step-by-step manner to determine the gel sufficiency parameter with respect to each of the areas 401-416, while the probe 112 collects the physiological data of the subject. In such examples, the probe 112 is collecting the physiological data while the sensor 118 is determining the gel sufficiency parameter. This approach conserves time by collecting two types of data simultaneously.

At 220, the gel management circuit 128 determines that an amount of the gel 420 on an area (e.g., the area 401) of the skin is insufficient based on the gel sufficiency parameter. The gel management circuit 128 of the controller 120 determines that the amount of gel on an area is insufficient responsive to determining that the gel sufficiency parameter crosses a first threshold. For this determination, the gel sufficiency parameter measured with respect to any pair of metal contacts (e.g., the metal contact 320 and another one of the metal contacts 330-350 when the angle of incidence α is above the threshold as described) having the scalar 0 is ignored. The pairs of metal contacts having the scalar 1 are taken into account and are referred to as "candidate pairs." In other examples, any two of the metal contacts 330-350 constitute a candidate pair regardless of the angle of incidence (e.g., the scalar is not applied). In some examples, in response to determining that one, a majority of, or all of the candidate pairs have a gel sufficiency parameter that crosses the first threshold (e.g., exceeds or is below the first threshold based on a type of gel sufficiency parameter), the amount of gel is determined to be insufficient. In the example in which the gel sufficiency parameter is a signal indicative of the resistance measured by the sensor 118, the first threshold is a threshold resistance. The measured resistance being above the threshold resistance means that the gel is insufficient. An example threshold resistance is between 0 ohm or an error/noise margin (e.g., 0.01 ohm, 0.05 ohm, 0.1 ohm, 1 ohm, and so on) and 1000 ohms. Another example threshold resistance is between 0 ohm or an error/noise margin (e.g., 0.01 ohm, 0.05 ohm, 0.1 ohm, 1 ohm, and so on) and 1500 ohms. Yet another example threshold resistance is between 0 ohm or an error/noise margin (e.g., 0.01 ohm, 0.05 ohm, 0.1 ohm, 1 ohm, and so on) and 1500 ohms.

In the example in which the gel sufficiency parameter is a signal indicative of the conductance or conductivity measured by the sensor 118, the first threshold is a threshold conductance or a threshold conductivity. The measured conductance or conductivity being below the threshold conductance or the threshold conductivity means that the gel is insufficient. An example threshold conductance is 10 mS. Another example threshold conductance is 12 mS.

In the example in which the gel sufficiency parameter is a signal indicative of the capacitance measured by the sensor 118, the first threshold is a threshold capacitance. The measured capacitance being below the threshold capacitance means that the gel is insufficient. An example threshold capacitance is between 100-200 pF.

At 230, in response to determining that the amount of gel on the area of the skin is insufficient, the robotics control circuit 126 controls the applicator 116 to apply an additional amount of gel on that area of the skin. For example, the robotics control circuit 126 can control the applicator 116 to move gel from another (second) area (e.g., an area with superfluous gel or a random area) to the area that is lacking gel.

In some arrangements, the second area is another area in the workspace 400 that is selected randomly by the gel management circuit 128. For example, responsive to determining that the area 401 lack gel (per block 220), another area in the workspace 400 is randomly selected to be the second area. In some instances, an area (e.g., the areas 402-405, 408, 409, 412, and 413-416) on the edge of the workspace 400 is selected, given that due to the operations of the probe 112, extra gel typically aggregate on the edge of the workspace 400.

In some arrangements, the second area is known to have extra gel. For example, the system 100 may include a gel dispenser (not shown) configured to deposit gel in a given area (e.g., the area 404) of the workspace 400 periodically or continuously. Therefore, the area (e.g., a gel reservoir) on which gel is known to be deposited can be selected as the second area. In another example, the gel reservoir may be an area in which an operator manually applies and/or replenishes the gel. In yet another example, the gel reservoir may be an area in which superfluous gel is present for any suitable reason.

The gel management circuit 128 of the controller 120 is configured to determine that the amount of gel on an area is superfluous responsive to determining that the gel sufficiency parameter exceeds a second threshold. For example, the system 100 may include a light source configured to shine light (e.g., an infrared (IR) light on the workspace) and a light sensor configured to detect reflected light from the workspace 400 (including the second area). The light may be at an angle of incidence (e.g., 30°, 45°, 60°, and the like) relative to the workspace 400. In some examples, the light sensor may be a camera configured to capture image data of workspace 400. The gel management circuit 128 is configured to analyze the reflected light or perform image processing on the image data to determine a reflective signature information (e.g., an IR reflective signature information, which is the gel sufficiency parameter in this case) for the workspace 400. The reflective signature information may include directions of the reflected light, intensity of the reflected light, and another attributes. The second threshold can be a reflective signatures threshold (e.g., an IR reflective signature threshold), such that any area in the workspace 400 that has an IR reflective signature above the IR reflective signature threshold can be the second area. In some examples, the area in the workspace 400 that has the largest IR reflective signature is selected to be the second area. In some examples, an additive can be added to the gel to improve reflection. Examples of the additive include but are not limited to, infrared reflecting pigments, infrared reflective paints, glass, glass bubbles, infrared reflecting coatings, and so on.

In some arrangements, instead of or in addition to the IR reflective signature information, the gel management circuit 128 is configured to perform image processing on the image data to determine maximally stable extremal regions (MSER) information for each area in the workspace 400 with respect to exposed skin of the subject that does not have any gel there on. In that regard, the camera is also configured to capture image data of the skin of the subject outside of the workspace 400. The second threshold can be an MSER threshold, such that any area in the workspace 400 that has an MSER above the MSER threshold can be the second area. In some examples, the area in the workspace 400 that has the largest MSER is selected to be the second area.

The robotics control circuit 126 configures the robotics 114 to translate the applicator 116 from the second area to the first area by controlling the robotics 114 to move the applicator 116 to be over the second area, extend the applicator 116 toward the skin in response to the robotics control circuit 126 determining that the applicator 116 is over the second area, orient a gel retaining surface of the applicator 116 to face a direction of the first area (e.g., the area 401) by tilting the applicator 116 to a tilted position, and move the applicator 116 from the second area to the first area while the applicator 116 is in the tilted position.

In some examples, the tilted position refers to tilting the applicator 116 (e.g., the probe 112) to an angle of incidence α (e.g., less than a maximum allowable degree such as but not limited to, 15°, 20°, 25°, and so on), as shown in FIG. 3B. In some examples, the gel management circuit 128 can determine the amount of tilt (e.g., the angle of incidence α) based on (proportional to) the amount of gel on the area. For example, the more gel is to be moved, the more tilt (the larger the angle of incidence α) is. A larger angle of incidence α allows more gel to be received in the concave surface 360.

FIGS. 5A-5D are schematic diagrams illustrating an example method for managing gel according to various arrangements. Referring to FIGS. 1-5D, FIGS. 5A-5D pertains to the arrangements in which the probe 112 itself is the applicator 116. FIG. 5A illustrate an example implementation of block 210, with the probe 112 being perpendicular to skin 500 of the subject as described with respect to FIG. 3A. The metal contacts 320-350 are not shown for clarity. FIG. 5A shows that the sensor 118 on the probe 112 detects that the gel on the area 401 is insufficient in some examples.

Figure 6:
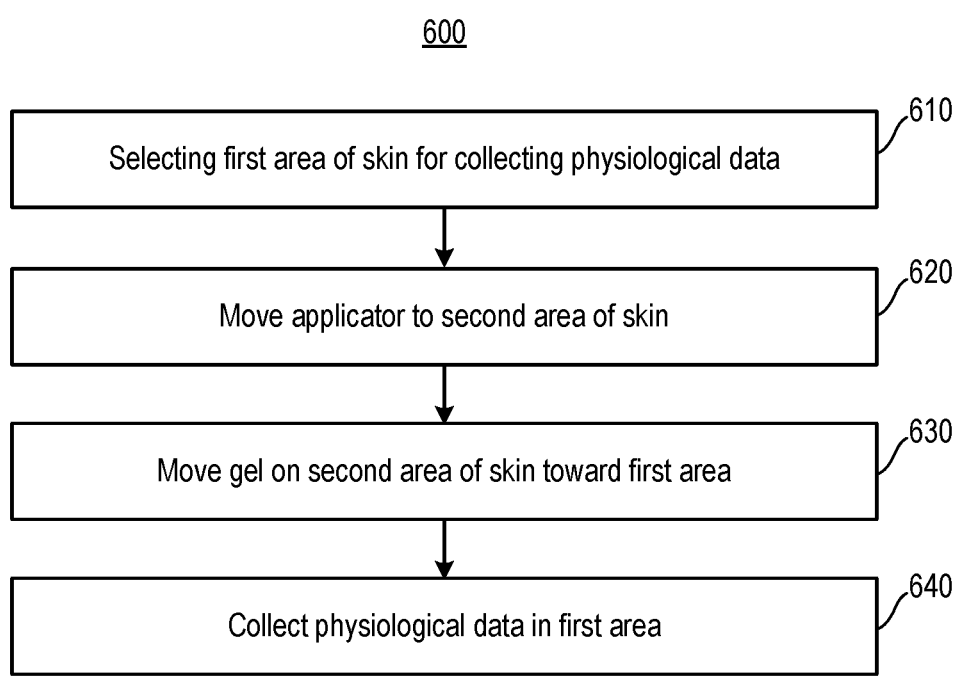
FIG. 6 is a flowchart diagram illustrating an example method for managing gel on a subject according to various arrangements.
Figure 7:
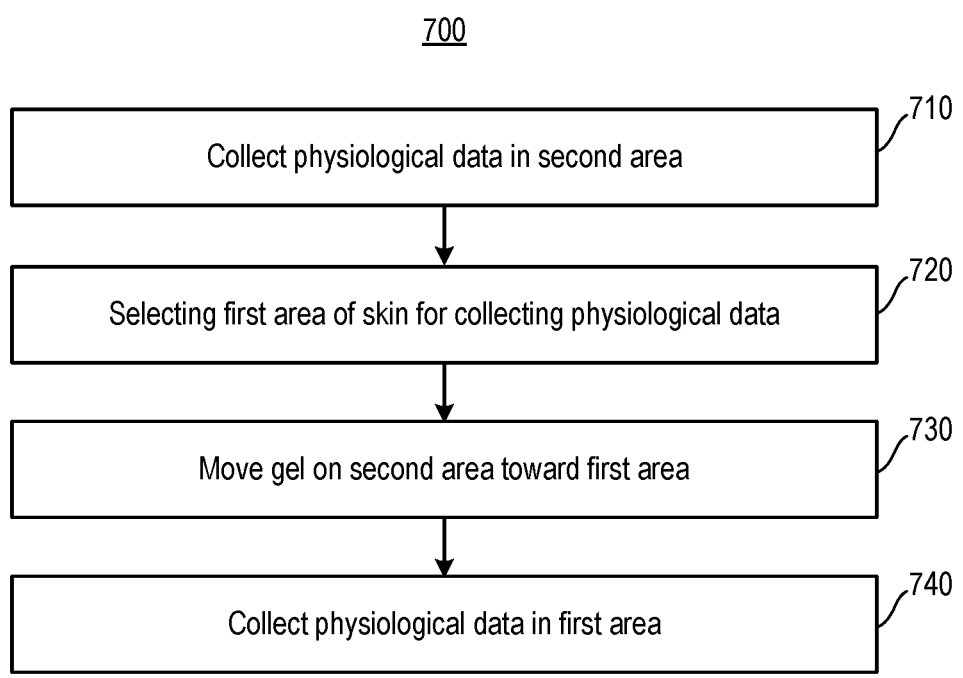
FIG. 7 is a flowchart diagram illustrating an example method for managing gel on a subject according to various arrangements.

In other examples, the gel can be moved without such detection as shown in FIG. 5A. FIGS. 6 and 7 show methods 600 and 700 corresponding to moving the gel without detecting that the gel is insufficient.

FIGS. 5B-5D illustrate an example implementation of block 230, showing an example by which an additional amount of gel can be applied. For example, the gel sufficiency parameter for the area 401 is determined to be below the first threshold, indicating that the area 401 has an insufficient amount of gel 420. The area 413 is selected to be the second area based on any suitable method described herein. The gel management circuit 128 relates such information to the robotics control circuit 126. The information includes but is not limited to, coordinates of the area 401, a "gel needed" indicator associated with the coordinates of the area 401, coordinates of the area 413, and an "excess gel" indicator associated with the coordinates of the area 413.

The robotics control circuit 126 is configured to control the applicator 116 (the probe 112) to apply the additional gel from the area 413 to the area 401 by controlling the robotics 114 to translate the applicator 116 (the probe 112) from the area 413 to the area 401. For example, the robotics control circuit 126 is configured to control the robotics 114 to retract the applicator 116 (the probe 112) away from the skin 500 when the applicator 116 (the probe 112) is at the area 401 and to move the applicator 116 (the probe 112) to be over the area 413, as shown in FIG. 5B.

In response to the robotics control circuit 126 determining that the applicator 116 (the probe 112) is adjacent to (e.g., over) the area 413 as shown in FIG. 5B, the robotics control circuit 126 configures the robotics 114 to extend the applicator 116 (the probe 112) toward the skin 500 to be in contact with the skin 500 on the area 413. The robotics control circuit 126 configures the robotics 114 to orient the gel retaining surface of the applicator 116 (the probe 112) to face a direction of the first area (e.g., the area 401) by tilting the applicator 116 (the probe 112) to a tilted position as shown in FIG. 5C. In some examples, the tilted position refers to tilting the applicator 116 (e.g., the probe 112) to an angle of incidence α (e.g., less than a maximum allowable degree such as but not limited to, 15°, 20°, 25°, and so on), as shown in FIG. 3B. In some examples, the gel management circuit 128 can determine the amount of tilt (e.g., the angle of incidence α) based on (proportional to) the amount of gel on the area. For example, the more gel is to be moved, the more tilt (the larger the angle of incidence α) is. A larger angle of incidence α allows more gel to be received in the concave surface 360. The gel retaining surface of the applicator 116 is the concave surface 360 of the probe 112. As shown in FIG. 5C, the concave surface 360 of the probe 112 faces toward the area 401.

Then, the robotics control circuit 126 is configured to control the robotics 114 to move the applicator 116 (the probe 112) from the area 413 to the area 401 across the skin 500 while the applicator 116 (the probe 112) is in the tilted position with the additional gel, as shown in FIG. 5D. At least a portion of the applicator 116 (the probe 112) contacts the skin 500 as the applicator 116 (the probe 112) is being moved across. As such, additional gel is applied to the area 401.

Additional gel can be moved in a similar manner in the arrangements in which the applicator 116 is different from the probe 112, with the robotics 114 or another suitable set of robotics moving the applicator 116.

FIG. 6 is a flowchart diagram illustrating an example method 600 for managing gel on a skin of a subject according to various arrangements. Referring to FIGS. 1-6, the method 600 is concerned with moving gel from a second area preemptively before collecting of the physiological data on the first area, without determining whether the gel is insufficient in the first area.

At 610, the controller 120 is configured to select a first area (e.g., the area 401) of the skin 500 for collecting the physiological data. In some examples, the first area may be a next step in a series of steps taken to collect the physiological data in the workspace 400. That is, in a previous step, the probe 112 has collected the physiological data in an area (e.g., the area 402 or 405) adjacent to the first area (e.g., the area 401).

At 620, the robotics control circuit 126 is configured to move the applicator 116 (the probe 112) to a second area of the skin. In some arrangements, the second area is another area in the workspace 400 that is selected randomly by the gel management circuit 128 in the manner described. In some arrangements, the second area is known to have extra gel (due to operations of a gel reservoir) in the manner described. In some arrangements, the second area is determined to have superfluous gel using IR reflective signature and/or MSER as described.

At 630, the robotics control circuit 126 is configured to move gel on the second area of the skin toward the first area, for example, in the manner described with respect to FIGS. 5B-5D. At 640, the probe 112 is configured to collect the physiological data in the first area. That is, gel is preemptively moved to the first area before collection of the physiological data. In some examples, the method 600 is executed for every step (area) in a series of steps for collecting the physiological data in the workspace 400. In some examples, the method 600 is executed every N steps in the series of steps for collecting the physiological data in the workspace 400. In some examples, the method 600 is executed periodically (e.g., every N seconds) when the probe 112 is collect the physiological data the workspace 400. In some examples, the method 600 is executed based on distance traveled (e.g., every N cm) when the probe 112 is collect the physiological data the workspace 400.

FIG. 7 is a flowchart diagram illustrating an example method 700 for managing gel on a subject according to various arrangements. The method 700 is concerned with moving gel to a first area (e.g., the area 401), which is a next step in a series of steps taken to collect the physiological data in the workspace 400. Currently, the probe 112 is collecting the physiological data in a second area, which is a current step in the series of steps. The probe 112 is provided (e.g., installed, structurally supported, or otherwise enabled for movement) prior to the method 700. The probe 112 is the applicator 116, meaning that the probe 112 can move the gel as well as collect the physiological data.

At 710, the probe 112 is configured to the physiological data in the second area. The second area may be an area (e.g., the area 402 or 405) adjacent to the first area (e.g., the area 401).

At 720, the controller 120 is configured to select the first area (e.g., the area 401) for collecting the physiological data. As described, the first area may be a next step (after the second area) in a series of steps taken to collect the physiological data in the workspace 400.

At 730, the robotics control circuit 126 is configured to move gel on the second area toward the first area, responsive to the data collection in the second area having concluded. For example, the robotics control circuit 126 configures the robotics 114 to translate the probe 112 from the second area to the first area by controlling the robotics 114 to tilt the probe 112 in a tilted position in the manner described while the probe 112 is in the second area and moving the probe 112 to the first area in the tilted position while contacting the subject. That is, the robotics control circuit 126 configures the robotics 114 to orient the gel retaining surface (the concave surface 360) of the probe 112 to face a direction of the first area (e.g., the area 401) by tilting the probe 112 to the tilted position. In some examples, the tilted position refers to tilting the probe 112 to an angle of incidence α (e.g., less than a maximum allowable degree such as but not limited to, 15°, 20°, 25°, and so on). In some examples, the gel management circuit 128 can determine the amount of tilt (e.g., the angle of incidence α) based on (proportional to) the amount of gel on the second area. For example, the more gel is to be moved, the more tilt (the larger the angle of incidence α) is. A larger angle of incidence α allows more gel to be received in the concave surface 360.

At 740, the probe 112 is configured to collect the physiological data in the first area. That is, gel is preemptively moved to the first area before collection of the physiological data. In some examples, the method 700 is executed for every step (area) in a series of steps for collecting the physiological data in the workspace 400. In some examples, the method 700 is executed every N steps in the series of steps for collecting the physiological data in the workspace 400. In some examples, the method 700 is executed periodically (e.g., every N seconds) when the probe 112 is collect the physiological data the workspace 400. In some examples, the method 700 is executed based on distance traveled (e.g., every N cm) when the probe 112 is collect the physiological data the workspace 400.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of blocks in the processes disclosed is an example of illustrative approaches. Based upon design preferences, it is understood that the specific order or hierarchy of blocks in the processes may be rearranged while remaining within the scope of the previous description. The accompanying method claims present elements of the various blocks in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the blocks of various examples must be performed in the order presented. As will be appreciated by one of skill in the art the order of blocks in the foregoing examples may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm blocks described in connection with the examples disclosed herein may be implemented as electronic hardware, computer software, or combinations of both. To clearly illustrate this interchangeability of hardware and software, various illustrative components, blocks, modules, circuits, and blocks have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

It should be noted that although the diagrams herein may show a specific order and composition of method blocks, it is understood that the order of these blocks may differ from what is depicted. For example, two or more blocks may be performed concurrently or with partial concurrence. Also, some method blocks that are performed as discrete blocks may be combined, blocks being performed as a combined block may be separated into discrete blocks, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web arrangements of the present disclosure could be accomplished with standard programming techniques with rule based logic and other logic to accomplish the various database searching blocks, correlation blocks, comparison blocks, and decision blocks.

What is claimed is:

1. A system for managing gel on a subject, comprising:
a transducer;
a controller configured to control the transducer to move the gel to a first area of the subject from a second area of the subject; and
a sensor configured to output a gel sufficiency parameter for the gel on the subject, wherein:
the controller is configured to determine that a first amount of the gel on the first area is insufficient based on the gel sufficiency parameter;
the controller is configured to select the second area of the subject based on the second area being proximate to and at an edge of the first area of the subject; and
the controller is configured to move a second amount of the gel to the first area from the second area in response to determining that the first amount of the gel on the first area is insufficient and in response to selecting the second area of the subject.

2. The system of claim 1, wherein the controller is configured to determine that the second amount of gel on the second area is above a threshold.

3. The system of claim 2, further comprising a camera configured to capture image data of the second area, wherein the controller is further configured to determine that the second amount of gel on the second area is above an infrared (IR) reflective signature threshold based on an IR reflective signature information determined based on the image data.

4. The system of claim 2, further comprising a camera configured to capture image data of the second area, wherein the controller is further configured to determine that the second amount of gel on the second area is above a maximally stable extremal regions (MSER) threshold based on MSER information determined based on the image data.

5. The system of claim 1, wherein the controller determines that the first amount of the gel on the first area is insufficient responsive to determining that the gel sufficiency parameter is below a threshold.

6. The system of claim 1, wherein the gel sufficiency parameter is a resistance between two metal contacts of the sensor.

7. The system of claim 1, wherein the gel sufficiency parameter is a conductance or conductivity between two metal contacts of the sensor.

8. The system of claim 1, wherein the sensor is on the transducer.

9. The system of claim 1, wherein
the system further comprises robotics configured to move the transducer;
the controller is configured to control the transducer to move the gel by controlling the robotics to translate the transducer from the second area to the first area.

10. The system of claim 9, wherein the controller configures the robotics to translate the transducer from the second area to the first area by controlling the robotics to:
move the transducer to be over the second area;
extend the transducer toward the subject in response to the controller determining that the transducer is over the second area;
orient a gel retaining surface of the transducer to face a direction of the first area by tilting the transducer to a tilted position; and
move the transducer from the second area to the first area while the transducer is in the tilted position.

11. The system of claim 9, wherein the controller configures the robotics to translate the transducer from the second area to the first area by controlling the robotics to:
tilt the transducer in a tilted position while the transducer is in the second area; and
moving the transducer to the first area in the tilted position while contacting the subject.

12. The system of claim 9, wherein the controller configures the robotics to translate the transducer from the second area to the first area by controlling the robotics to move the transducer from the second area to the first area across the subject.

13. The system of claim 1 wherein
a workspace of the transducer comprises a plurality of areas; and
the plurality of areas comprises the first area and the second area.

14. The system of claim 13, wherein the workspace corresponds to a temporal region of a head of the subject.

15. The system of claim 13, wherein the plurality of areas corresponds to steps by which the transducer is configured to move.

16. The system of claim 13, wherein the controller selects the second area randomly from the plurality of areas.

17. The system of claim 1, wherein the second area is a gel reservoir.

18. The system of claim 1, wherein
the controller is configured to control the transducer to move the gel to the first area of the subject from the second area of the subject by orienting the transducer to a tilted position such that a bottom surface of the transducer pushes the gel towards the first area.

19. The system of claim 18, wherein the controller is configured to orient the transducer from a flat position to the tilted position.

20. A method for managing gel on a subject, comprising:
controlling, by a controller, a transducer to move the gel to a first area of the subject from a second area of the subject;
outputting, by a sensor, a gel sufficiency parameter for the gel on the subject;
determining, by the controller, that a first amount of the gel on the first area is insufficient based on the gel sufficiency parameter;
selecting, by the controller, the second area of the subject based on the second area being proximate to and at an edge of the first area of the subject; and
controlling, by the controller, the transducer to move a second amount of the gel to the first area from the second area in response to determining that the first amount of the gel on the first area is insufficient and in response to selecting the second area of the subject.

21. The method of claim 20, wherein controlling the transducer to move the gel to the first area from the second area comprises
moving the transducer to be over the second area;
extending the transducer toward the subject in response to the controller determining that the transducer is over the second area;
orienting a gel retaining surface of the transducer to face a direction of the first area by tilting the transducer to a tilted position; and moving the transducer from the second area to the first area while the transducer is in the tilted position.

\* \* \* \* \*